United States Patent [19]
Farzin-Nia

[11] Patent Number: 5,829,972
[45] Date of Patent: Nov. 3, 1998

[54] PLASTIC ORTHODONTIC APPLIANCE HAVING IMPROVED BONDING CHARACTERISTICS

[75] Inventor: Farrokh Farzin-Nia, Inglewood, Calif.

[73] Assignee: Ormco Corporation, Glendora, Calif.

[21] Appl. No.: 626,355

[22] Filed: Apr. 2, 1996

[51] Int. Cl.⁶ .................................................. A61C 7/16
[52] U.S. Cl. .................................................. 433/9; 433/8
[58] Field of Search ............................................. 433/8, 9

[56] References Cited

U.S. PATENT DOCUMENTS

| | | | |
|---|---|---|---|
| D. 290,040 | 5/1987 | Kelly | D24/16 |
| 4,068,379 | 1/1978 | Miller et al. | |
| 4,165,561 | 8/1979 | Miller et al. | |
| 4,661,059 | 4/1987 | Kanno | 433/9 |
| 4,927,361 | 5/1990 | Smith et al. | |
| 5,108,285 | 4/1992 | Tuneberg | 433/9 |
| 5,254,002 | 10/1993 | Reher et al. | |
| 5,267,854 | 12/1993 | Schmitt | 433/9 |
| 5,295,823 | 3/1994 | Farzin-Nia | |
| 5,522,725 | 6/1996 | Jordon et al. | 433/9 |
| 5,622,494 | 4/1997 | Andrako et al. | 433/9 |

*Primary Examiner*—Paul J. Hirsch
*Attorney, Agent, or Firm*—Wood, Herron & Evans, L.L.P.

[57] ABSTRACT

Plastic orthodontic appliances having improved bonding characteristics are described. The appliances have a polymeric base with projecting structure extending outwardly therefrom and an applied coating of a chemically activatable material. The projecting structure includes a broadened outer extremity and undercuts proximate the outer extremity which form mechanical bonds with a bonding adhesive. The chemically activatable material applied to the projecting structure increases the chemical bond between the structure and the bonding adhesive and thereby enhances the overall bonding characteristics of the appliance. Another aspect of the invention concerns a method of enhancing the bond strength of plastic orthodontic appliances. The method includes applying a chemically activatable material layer by sputtering, plasma deposition, or other deposition process, to a plastic orthodontic appliance having projecting structure. In a preferred embodiment, the projecting structure is a plurality of posts, and the chemically activatable coating is $SiO_2$. It is further contemplated that the chemically activatable coating may be activated by treatment with silane.

20 Claims, 6 Drawing Sheets

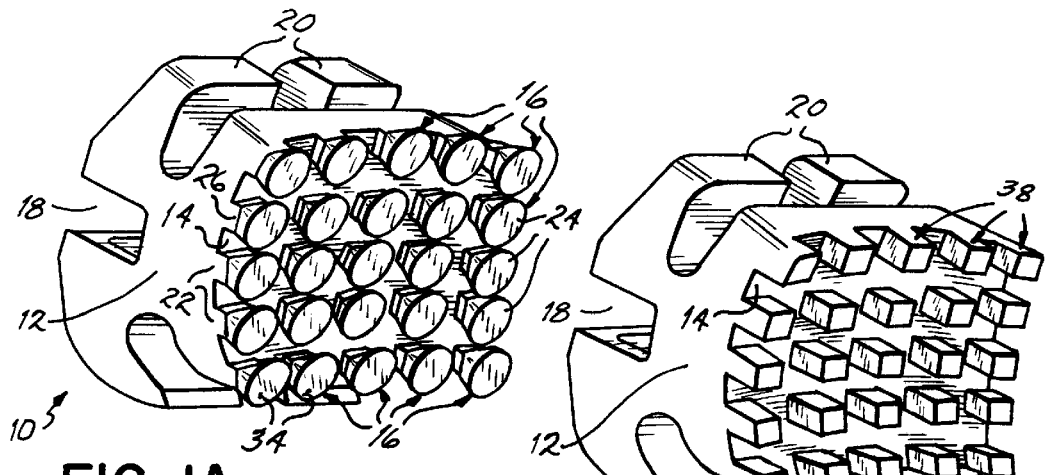
FIG. 1A
FIG. 1B
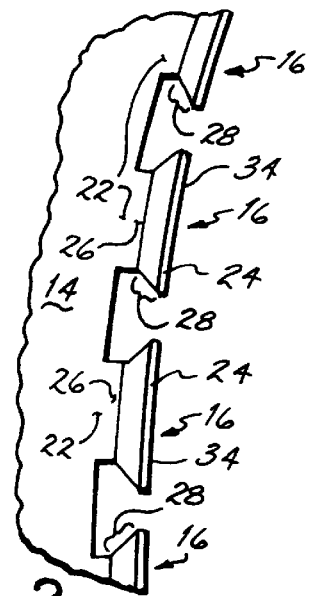
FIG. 2
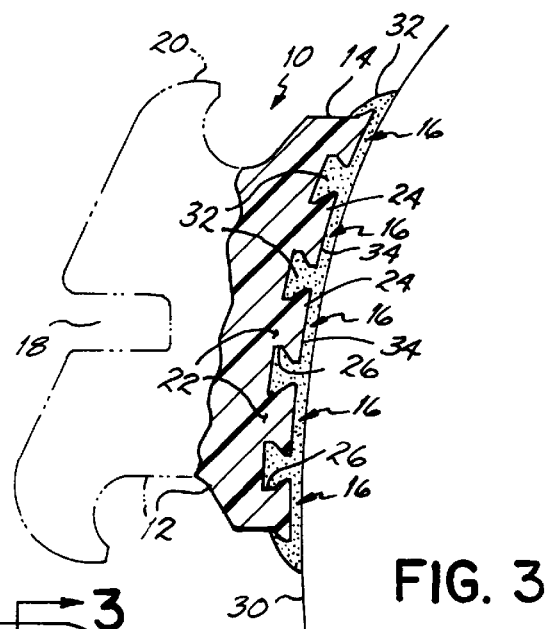
FIG. 3
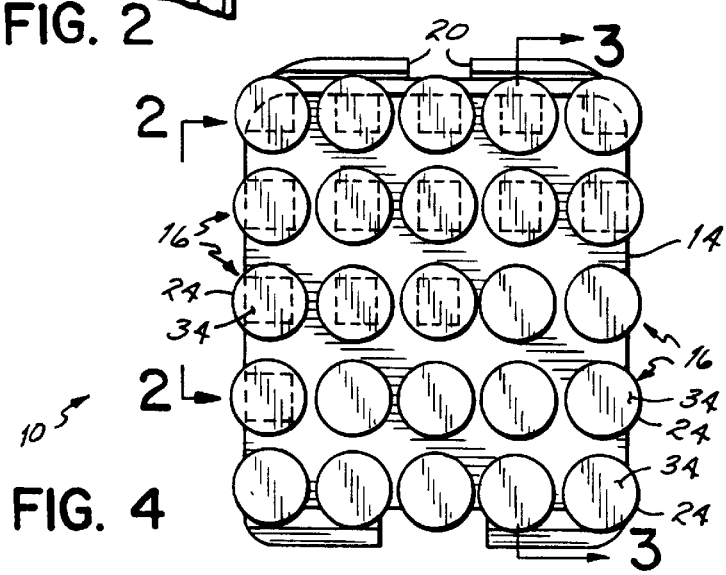
FIG. 4

PLASTIC ORTHODONTIC APPLIANCE HAVING IMPROVED BONDING CHARACTERISTICS

FIELD OF THE INVENTION

This invention is directed to orthodontic appliances, and more particularly to plastic orthodontic appliances having projecting structures extending outwardly from the appliance bonding base with an applied layer of a chemically activatable material. The appliances of the present invention have improved bonding characteristics and are designed for attachment directly to the teeth of a patient; the invention also encompasses methods of making such appliances.

BACKGROUND OF THE INVENTION

In the field of orthodontics, it is known to bond orthodontic appliances, such as brackets, buccal tubes and the like, to a tooth surface with an adhesive. Typically, this is accomplished by chemically bonding an appliance to a tooth surface using an adhesive. The bonding of orthodontic appliances to teeth is of critical importance for several reasons: 1) to insure proper transfer of forces directly to the teeth; 2) to insure that no undue forces are exerted on the teeth, particularly during removal of the appliances, which may cause removal of enamel; and 3) to insure that the appliances are not unintentionally debonded prior to completion of the treatment.

With respect to orthodontic brackets having a metal bonding surface, various solutions have been suggested in the prior art to provide or enhance the bonding characteristics of the appliance. For example, U.S. Pat. Nos, 4,165,561 and 4,068,379 disclose the use of a metal mesh welded to the bonding base of the appliance in order to provide acceptable mechanical bonding characteristics. U.S. Pat. No. 4,927,361 suggests the use of particles in order to provide a porous structure on the tooth contact surface of the appliance. However, these types of brackets are made of materials which are substantially non-chemically reactive, and thus are limited with respect to the bond strengths that can be obtained since they rely on the mechanical bonding characteristics of the bracket.

The bonding characteristics of a metal orthodontic bracket may be improved by incorporating a primary mechanical interlock retainer including undercut regions which have the capability of providing adequate bond strength when adhered to a tooth enamel surface using a dental adhesive, and a secondary mechanical bond strength enhancement applied to the undercut regions. The secondary mechanical bond strength enhancement provides additional undercut regions to enhance the mechanical bond strength by increasing the surface area of the primary undercut regions. The surface area may be increased by surface etching or roughening or by adhering particles to the primary retention means.

U.S. Pat. No. 5,295,823, herein incorporated by reference, discloses a method of bonding particles to a metallic bonding base of an orthodontic appliance. U.S. Pat. No. 5,295,823 discloses a primary retention surface of a mesh, a layer of metallic or non-metallic particles (such as spheres, rods, shards, etc.) or groups including undercuts formed in the tooth contact surface. U.S. Pat. No. 5,295,823 also discloses secondary enhancement treatments including surface roughening, particles on the order of 5 to 200 micron flame spray coated on the primary retention surface, and a chemically activatable material, such as $SiO_2$, deposited on the primary retention surface. Also disclosed is chemical activation of the chemically activatable material, such as silanation of $SiO_2$.

With respect to non-metal brackets, e.g., brackets made of a ceramic material, bonding of the brackets generally incorporates the use of a chemical treatment so that high bond strengths between bracket and tooth are obtained. However, use of chemically reactive bonding adhesives generally requires special handling and care in order to obtain desired bonding strengths, as set forth in U.S. Pat. No. 4,681,538. Additionally, due to the high bond strengths obtained with ceramic-type brackets, and the manner in which the bonds are fractured, a much higher risk is presented that enamel may be removed from the tooth during bracket removal.

U.S. patent application Ser. No. 08/391,663, filed Feb. 21, 1995, herein incorporated by reference in its entirety, discloses a plastic orthodontic appliance having projecting structures extending outwardly from an appliance bonding base. Preferably the projecting structures are either a plurality of discreet projections, posts, or ridges or a single elongated continuous projection or ridge, which incorporates undercuts at its extremity to enhance mechanical bonding of the appliance to a tooth.

With respect to plastic brackets, other attempts have been made to improve the bonding characteristics thereof. For example, plastic brackets with flat bonding bases have been coated with $SiO_2$ and then silanated. However, such treatment has not resulted in any significant improvement in bond strength.

SUMMARY OF THE INVENTION

The present invention is intended to overcome the various shortcomings and drawbacks discussed above with respect to bonding orthodontic appliances to teeth and also provides improved bonding characteristics for appliances of the type disclosed in the referenced '663 application. More particularly, the invention encompasses improved orthodontic appliances and methods of making such appliances which result in improved bonding characteristics without presenting any substantially increased risk of removing enamel from the tooth. Another advantage of the present invention over the prior art is that substantially all adhesive is removed from the tooth enamel when the appliance is removed.

In its broadest aspects, this invention is directed to a method for forming an orthodontic appliance, and the appliance so formed. The appliance includes projecting structures extending from an appliance base, such as the bonding base, which are adapted to provide mechanical bonding of the appliance to a tooth surface utilizing an adhesive. The method includes injection molding a thermoplastic orthodontic appliance having a bonding base from which projecting structure(s) outwardly extend. The projecting structures have an inner extremity and an outer extremity, with the inner extremity being integrally connected to the appliance base. The process further includes softening the outer extremity of the plurality of discrete outer ends, and applying pressure thereto while in a softened state so as to deform the projecting structure and provide undercuts proximate the outer extremity for facilitating mechanical bonding of the appliance base to a tooth surface. The deformed outer extremities are then coated with a chemically activatable material, preferably an oxide of silicon, such as $SiO_2$. Ion beam deposition and plasma coating are two suitable techniques for providing the coating. The chemically activatable material is then activated by, for example, treatment with silane ($Si_nH_{2n+2}$). Adhesion bond strength of polymer brackets having projections with undercut regions is significantly improved by the combination of $SiO_2$ coating followed by silanation.

In one specific aspect of the invention, after forming a bracket or other appliance with a plurality of projections, the undercut portions are formed by softening and reshaping the projections. The softening step may be accomplished by transferring energy, such as heat or ultrasonic energy, to the outer extremity of the projecting structure. If heat transfer is used, heat may be transferred conductively to the outer extremity of the projecting structure by contacting the outer extremity with an external heat source such as a heating element or the like. In order to soften the projecting structures, the heating element should have a temperature above the glass transition temperature of the plastic. The thermoplastic orthodontic appliance typically is formed of a glass-filled polycarbonate material, in which case the heating element preferably has a temperature of from about 350° F. to about 400° F., more preferably about 390° F.

In a preferred form of the method, the heating element has a substantially continuous smooth surface such that the same heating element may be used during the softening step regardless of the exact location of the projecting structures relative to the curved appliance base, minimizing alignment problems. Furthermore, a preferred heating element has a size and curvature such that, the heating element contacts the outer ends of the projections substantially simultaneously, with the configuration of the curvature of the heating element matching the curvature of the tooth surface to which the appliance base is to be mounted.

The pressure application step generally includes applying pressure to the outer extremity of the projecting structures in a direction along longitudinal axis thereof toward the base, thereby slightly compressing the projecting structure. This pressure application step deforms the softened outer extremity of the projecting structures into a substantially mushroom-shaped configuration to thereby provide undercuts proximate the outer extremity. In a preferred form of the invention, the pressure application step includes applying pressure substantially simultaneously to the outer ends of all of the projections. Preferably, the projecting structure is compressed in the range of about 0.001 inch to about 0.004 inch in length. In the preferred embodiment, the pressure is applied to the outer extremity of the projecting structure using a heating element, in which case the heat transfer step and pressure applying step may temporally overlap.

The projecting structure extending from the appliance may be of many different shapes and alignments. For example, a solid post or posts, a hollow tubular post or posts, or combinations thereof, may be used. Preferably, prior to deformation of the outer ends, each of the posts has a generally square cross-sectional area along its entire length. A cross-sectional dimension of about 0.015 inch by about 0.015 inch is preferable. In the preferred embodiment, the posts are located on an imaginary grid and are spaced such that the center-to-center distance from one post center to an adjacent post center is approximately 0.030 inch. Furthermore, the posts have a length of from about 0.005 inch to about 0.010 inch.

When the orthodontic appliance is formed as an orthodontic bracket, the plastic may include reinforcing glass fibers and may have a reinforcing insert proximate an archwire slot.

The invention further contemplates providing an orthodontic appliance (such as a bracket) having a plastic bonding base and the deformed posts, as described above, with a bond strength enhancement coating applied to the appliance, and particularly to the deformed posts. This coating is of a chemically activatable material, such as $SiO_2$, and is intended to ensure that at least the minimum shear bond strength is achieved. Generally speaking, the minimum shear bond strength that is considered adequate for orthodontic brackets, as tested on brackets adhered to yearling bovine enamel tooth surfaces, is approximately 6.0 kilograms of load. This figure is dependent upon several variables, including adhesive type, particular bracket base material, and enamel surface preparation, among other things.

The bond strength enhancement coating applied to the base, including projecting structures, serves to provide chemical bonding with the dental adhesive, thereby complementing the mechanical bonding of the appliance to a tooth enamel surface using a dental adhesive, to enhance the overall bonding of the appliance to a tooth enamel surface.

The chemically activatable material may be applied by any one of several well known processes, so long as the processing temperature does not exceed the softening point of the plastic. Such processes include sputtering, ion beam deposition, or plasma coating of the outer extremity of the bracket. The preferred chemically activatable material is silicon dioxide ($SiO_2$). After deposition of the chemically activatable material, the bracket is exposed to silane in order to activate the material.

It will be appreciated that in the context of the present invention the term "chemically activatable material" is intended to include any one or combination of many materials, and particularly useful are oxides of the following elements: silicon, aluminum, boron, titanium, magnesium, zirconium, potassium, calcium, and sodium. One particularly suitable material is silicon dioxide ($SiO_2$); however, virtually any glass oxide of the type typically used in glass manufacturing is suitable for use in the context of the present invention.

In addition, the plastic orthodontic appliance of this invention, including the coating of chemically activatable material, is compatible with typical orthodontic adhesives and does not require the use of a primer, thereby simplifying the bonding process. Because many traditional, smooth bonding base plastic brackets require a primer before an adhesive may be applied, an orthodontist usually must perform this additional step chairside. Furthermore, with prior art plastic brackets, the adhesive used must be able to form a chemical bond with the primer and bracket, thereby limiting the kinds of orthodontic adhesives that can be used. Because the inventive plastic appliance of the present invention utilizes both chemical and mechanical bonding, these problems are avoided.

Another advantage of the present invention is that the bond between the orthodontic appliance and the adhesive is stronger than the bond between the adhesive and tooth enamel. Thus when the appliance is removed/debonded from the tooth, substantially all of the adhesive remains on the appliance and essentially no adhesive is left on the surface of the tooth.

The inventive orthodontic appliance and method discussed above offer several benefits and advantages. For example, the appliance offers the strength of a mechanical bonding base, as well as the increased strength of chemical bonding, in an aesthetically pleasing orthodontic appliance. Whereas conventional mechanical bonding brackets are formed of a metal such as stainless steel, the inventive appliance is formed of an aesthetically pleasing thermoplastic such as polycarbonate, which typically has a translucent appearance. Furthermore, the method for forming the appliance is relatively simple and inexpensive in comparison with the known cold working methods presently used on metal brackets. Also, the cold working distorts the microstructure of the raised metal posts, whereas the plastic softening and pressure applying steps of the invention form undercuts in the thermoplastic posts without distorting the microstructure, thereby maintaining the structural integrity of the plastic material.

These and other features and advantages of the present invention will become apparent to persons skilled in the art with reference to the detailed description which follows, taken in combination with the drawings.

BRIEF DESCRIPTION OF THE DRAWINGS

FIG. 1A is a rear perspective view of an orthodontic bracket after the posts have been deformed to provide a mechanical bonding base;

FIG. 1B is a rear perspective view of an orthodontic bracket before the posts have been deformed;

FIG. 2 is an enlarged side elevation of the deformed posts of the orthodontic bracket of FIG. 4 taken along line 2—2 thereof;

FIG. 3 is a partial cross section of FIG. 4 taken along line 3—3 thereof, showing the bracket adhered to a tooth surface;

FIG. 4 is a rear plan view of the orthodontic bracket of FIG. 1A;

DETAILED DESCRIPTION OF THE INVENTION

Figure 6:
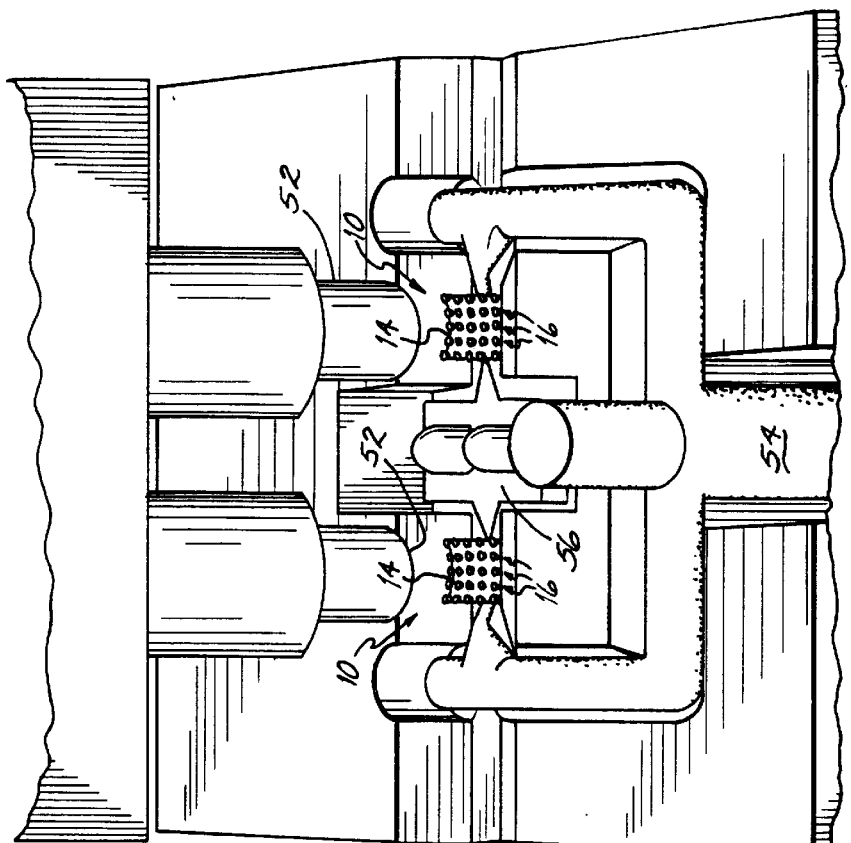
FIG. 6 is a closeup perspective view of the die of the projecting-structure deforming station shown in FIG. 5.

As used herein, the term "orthodontic appliance" refers to any device which is adhered to a tooth surface in conjunction with moving teeth or holding teeth in a particular position. Non-limiting examples include orthodontic brackets, buccal tubes and the like. The term "plastic" as used herein is meant to include plastic material whether or not reinforced with glass fibers or some other reinforcing material and/or other additives such as fillers, pigments, etc. In addition, the term "projecting structure" refers to any structure which extends outwardly from an orthodontic appliance bonding base and which may be deformed at its outer extremity, thereby forming an undercut proximate the outer extremity which is adapted to form a mechanical bond with an orthodontic adhesive when the adhesive cures. Non-limiting examples of projecting structure include a solid post or posts, a hollow tubular post or posts, or a combinations thereof.

Referring to FIG. 1A, a plastic orthodontic bracket 10 according to the principles of the invention includes a body 12 and a bracket base 14, with a plurality of posts 16 extending outwardly from the bracket base 14 in a grid-like pattern. The bracket further includes an archwire slot 18 and a pair of tie wings 20.

As shown in FIG. 2, each of the posts 16 has an inner end 22 integral with the bracket base 14, an outer end 24 and an intermediate section 26 disposed between the inner and outer ends 22, 24. Each post further includes an undercut 28 for forming a mechanical bond with an orthodontic adhesive.

Referring to FIG. 3, an orthodontic bracket 10 is shown bonded to a tooth surface 30 using an orthodontic bonding adhesive 32. Typically, an orthodontist will apply the adhesive 32 to the bracket base 14, allowing the adhesive to flow into and fill the open spaces between the posts 16 as well as cover the outer ends 24. The bracket 10 then may be placed on the tooth surface 30, and as the adhesive 32 cures, a chemical bond and a mechanical interlocking bond is formed between the adhesive 32 and the bracket 10 or other orthodontic appliance. A bond is also formed between the adhesive and the tooth surface. Undercuts 28 in the bracket cause the bracket 10 to more tightly bond to the tooth than a bracket having no undercut portion, thereby enhancing the adhesion of the bracket 10 to a tooth 30. Additionally, the posts 16 increase the surface area, enhancing the chemical bonding with the adhesive to the base. Furthermore, it is believed that the bond may be not only similar in strength (shear or tensile strength at bond failure at low strain rates) to mesh-based brackets, but also tougher (more impact resistant) than the bond for metal or ceramic brackets, because of the relative flexibility of the posts 16 and the inherent ductility of the plastic material.

Preferably, the plastic orthodontic appliance is formed of a polycarbonate reinforced with glass fibers as taught in U.S. Pat. No. 5,254,002, which is incorporated in its entirety by reference, with the fibers preferably being about 20%–40% by weight. The bracket may also include a reinforcing insert proximate the archwire slot, as also taught in the '002 patent.

In a preferred embodiment of the present invention, the appliance bonding base has a compound curvature corresponding to the curvature of a tooth surface. Furthermore, as shown in FIGS. 1A, 1B, and 3, the outer ends 24 of the posts 16, when viewed in combination, generally follow this same compound curvature, both before and after deformation.

As shown in FIG. 4, a preferred embodiment of the appliance has about 25 posts 16 arranged in a grid-like pattern. Each post has a square shaped cross-sectional area through its inner end 22 and intermediate section 26, with dimensions of about 0.015 inch×0.015 in. In addition, referring to FIG. 2, each broadened outer end 24 has a length of about 0.005 in. to about 0.010 in. from the inner end 22 to the tooth facing surface 34 of the broadened outer end 24. As further seen in FIG. 4, the spacing between post inner ends 22 is similar to the cross-sectional dimensions of the inner ends 22 themselves, ranging from about 0.010 in. to about 0.020 in.

Regardless of the particular configuration of the projecting structure employed, the space between adjacent portions of the deformed outer extremity of the projecting structure (for example, between adjacent broadened outer ends of an embodiment using discrete posts) must be sufficient to permit the adhesive to flow between the deformed adjacent portions into the undercut region below, which is a function of the adhesive viscosity and the method of application of the adhesive to the base.

In another embodiment (not shown) the appliance base has a centrally located area which is free of posts. This open area may be formed with an identifying mark, such as a letter or number, to assist in the identification of the appliance. The portions of the appliance base immediately adjacent to the open area may have partial posts, such as posts with smaller cross-sectional dimensions. While this embodiment slightly reduces the number of posts available for mechanical bonding, it still is able to form a strong mechanical interlock with an adhesive.

Typically, the orthodontic appliance is formed in a multi-step process. As shown best in FIG. 1B, a preferred bracket 10 or other appliance is molded having undeformed posts 38, and the broadened outer ends of the posts are formed in a secondary operation. The intermediate-stage appliance (having undeformed posts or other projecting structure) may be formed using a conventional thermoplastic molding technique as is taught by U.S. Pat. No. 5,254,002, preferably by injection molding.

Different molds may be used to achieve the desired sizing and distribution of undeformed posts or other projecting structure, and when an appliance having a plurality of posts is to be formed, preferably the mold is shaped so as to produce an appliance having post size and distribution as discussed above. Furthermore, the portion of the appliance mold used to make the undeformed posts or other projecting structure preferably has no draft (i.e., the walls of the cavities in the mold corresponding to the posts may be vertical as opposed to being tapered).

This ability to have vertical walls in the mold generally is not possible for a metal bracket having mechanical bonding posts because the greenware (molded metal bracket before sintering) is very fragile, and without tapered side walls in the mold that produce posts which have smaller cross-sectional dimensions toward their outer ends, some posts likely would break as the metal bracket is removed from the mold cavity. However, because the appliances of the present invention are formed of plastic, a mold having vertical side walls may be used without significant risk of projecting structure breakage. This feature provides enhanced strength to the posts or other projecting structure during both initial formation and subsequent broadening of the outer extremity. This feature also produces projecting structure having more material at its outer extremity relative to molded metal posts, thereby enlarging the undercuts and increasing the mechanical bonding area between the undercuts and the bonding adhesive.

While a preferred embodiment has been described in detail in the form of an orthodontic appliance having a projecting structure comprising a plurality of discrete posts, it will be appreciated that numerous alternative embodiments of the projecting structure may be provided.

Figure 5:
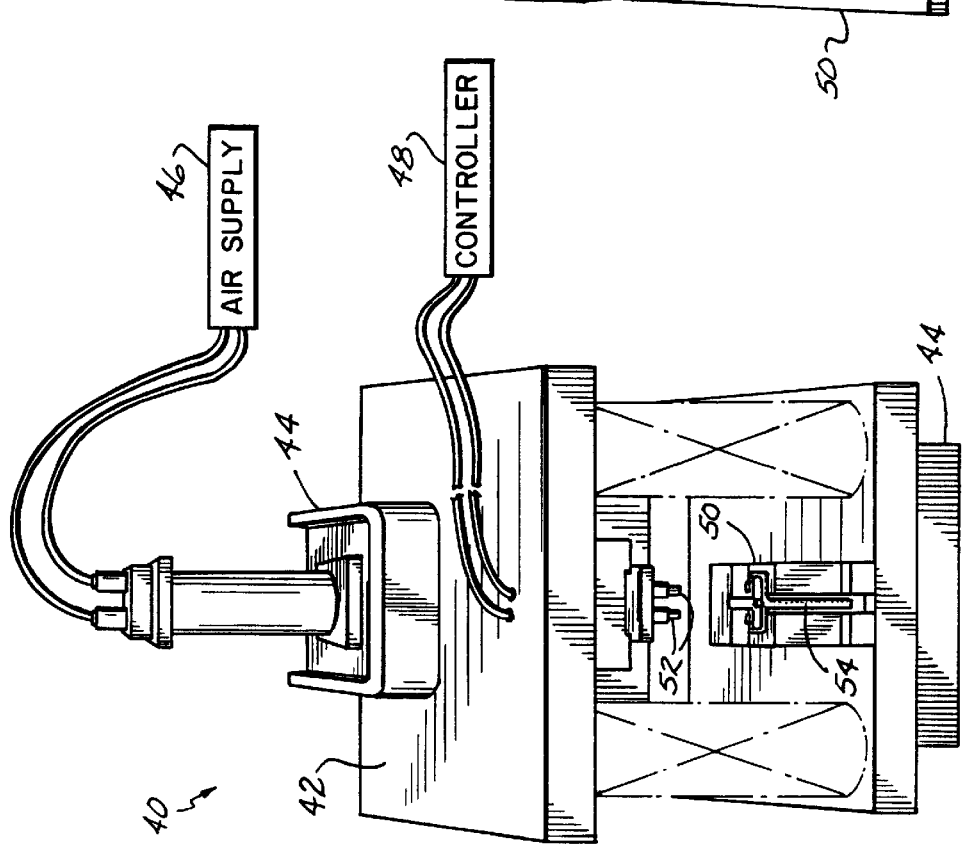
FIG. 5 is a perspective view of a projecting-structure deforming station used in a method of forming an orthodontic appliance.

In a preferred method of forming the orthodontic appliance, the posts or other projecting structure are deformed using a projecting-structure deforming station, a bench-scale version of which is shown in FIGS. 5 and 6. The post deforming station 40 broadly includes a die 42, arbor press 44, air supply 46 and controller 48 as shown in FIG. 5. More specifically, the die includes a holding fixture 50 for holding and positioning an orthodontic appliance or appliances, and a projecting-structure deforming tool 52 positioned directly above each appliance as shown in FIG. 6. The deforming tool 52 has a continuous smooth surface, therefore it may be used with appliances having different projecting structure location or density relative to the appliance base.

The deforming tool, because of a single continuous smooth surface rather than a plurality of discrete tools which must be precisely aligned to the appliance posts or other projecting structure, does not require critical positioning. Each deforming tool 52 has a compound curvature corresponding to the compound curvature of the tooth surfaces to which the appliance is to be mounted. Thus, the contour of the deformed extremity of the projecting structure matches the contour of the tooth surface. In the preferred projecting structure deforming method, the deforming tips are heated to a temperature which is high enough to bring the outer extremity of the projecting structure to its plastic softening point. When the orthodontic appliance is made of a reinforced polymer such as glass fiber-reinforced polycarbonate, the deforming tool temperature preferably ranges from about 350° F. to about 400° F., and more preferably about 390° F.

In a preferred method of forming the appliance, each heated deforming tool 52 moves downward in a substantially smooth and uniform motion toward the projecting structure of the corresponding appliance and a compressing force is applied to the projecting structure using the deforming tool 52. The projecting structure is softened almost instantly when it is contacted by the tool 52, and the tool 52 continues to advance in a downward compressing direction until it hits a positive hard stop (not shown). Once the deforming tool 52 reaches this hard stop, bias springs return the tool 52 to its original position. Typically, the force needed to move the heated deforming tool 52 downward is only slightly in excess of the force needed to overcome the bias on the return springs.

The deformed posts 16 then are allowed to cool and harden, and any sprue residue 54 is trimmed from each appliance. If the appliance is formed with a reinforcing insert, such as a ceramic or a metal insert, the main handling section 56 of the metal insert as shown in FIG. 6 may be trimmed from the appliance. Although thermal energy preferably is used to soften the undeformed posts, the posts may be softened using a number of other methods, such as ultrasonic energy, microwave energy and the like. Thermal energy is preferred, however, because it has been found to be easier to control the amount of deformation and the shape of the posts using this energy source.

It has been determined that applying a bond strength enhancement coating or treatment (hereinafter "bond strength enhancement treatment") to at least a portion of the projecting structure will enhance the overall bond strength characteristics of orthodontic bracket 10 when bonded to a tooth surface 30. It will be appreciated that the deposition procedures described below are equally applicable to the bracket 10 regardless of the specific projecting structure utilized (i.e., square solid posts, hollow cylindrical posts, etc.).

In a preferred embodiment, the bond strength enhancement treatment includes a deposited surface coating 39 which is formed by subjecting bracket 10 to a high energy surface treatment. More particularly, after the projection structure 16 has been deformed, bracket 10 is subjected to a sputtering, ion beam deposition, or a plasma coating step whereby small amounts of a chemically activatable material are deposited on the tooth facing surface 34 and the exposed areas of base 14. This procedure must be performed at a temperature less than the softening point of the plastic (approximately 300°–400° C.) to avoid melting or deforming the plastic. This procedure increases the overall bond strength of the bracket because, once the chemically activatable material is activated, there is improved chemical bonding with the various dental adhesives available. This chemical bonding, coupled with the mechanical bonding provided by the deformed projecting structure, enhances the overall bonding of the appliance.

Figure 7:
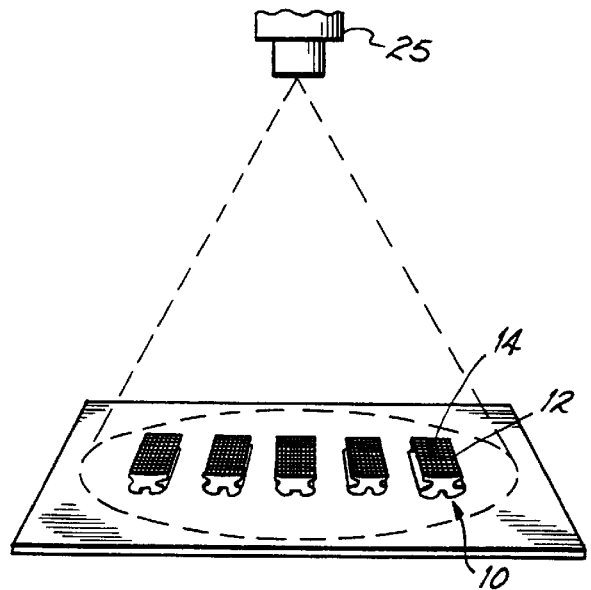
FIG. 7 is a perspective schematic representation of one coating step of the present invention.
Figure 8:
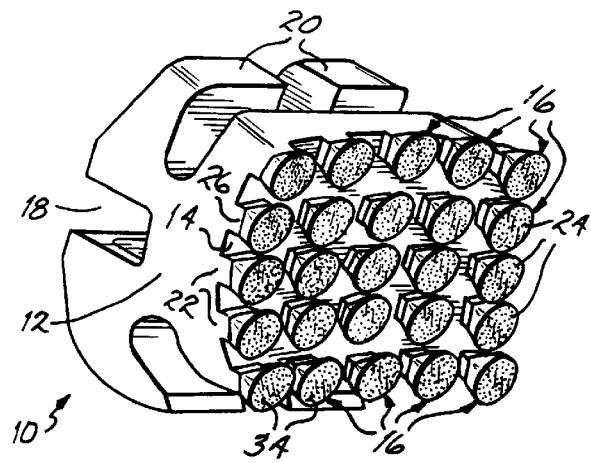
FIG. 8 is a rear perspective view of an orthodontic bracket after the posts have been deformed to provide a mechanical bonding base and after the coating step.
Figure 9:
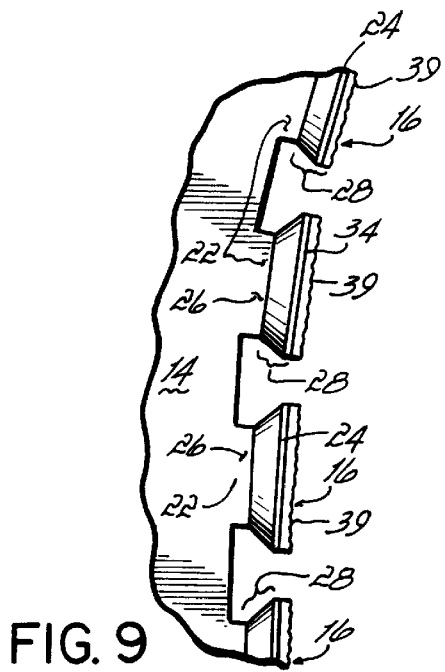
FIG. 9 is an enlarged side elevation of the deformed posts, after the coating step, of the orthodontic bracket of FIG. 8.

In one procedure, depicted schematically in FIG. 7, a plurality of brackets 10 (subsequent to deformation of the projection structure) are placed face down (the labial portion of the bracket facing downwardly) on a suitable support structure 17 such that the tooth facing surfaces 34 and 14 are exposed to a high energy source 25 located at a predetermined distance vertically above the brackets 10. High energy source 25 is activated and directs a stream of high energy ions toward the exposed surfaces of the bracket base 14 and tooth facing surfaces 34 of brackets 10.

In an alternative procedure (not explicitly shown), a plurality of brackets are placed in a basket and the basket is rotated in the path of the ion beam. In this way, statistically, every surface of the brackets is exposed to the ion beam which is a "line of sight" application. Thus the resulting brackets are coated over their entire exposed surface area with the chemically activatable material.

By way of specific example, a plurality of brackets 10 may be subjected concurrently to an ion beam deposition process whereby a $SiO_2$ coating is deposited on the exposed surfaces of the bracket base 14 or the entire bracket and tooth facing surfaces 34. This type of ion beam deposition is a procedure well known to persons skilled in the art and may utilize methods and apparatus commercially available from Spire Corporation of Bedford, Mass. More particularly, the typical parameters for the ion beam deposition of $SiO_2$ are as follows: silicon dioxide ions are directed to brackets 10 at 25 Kev and at an ion concentration of about $1 \times 10^{14}$ ions/cm$^2$ for approximately 2 hours. The resultant coating formed by this ion beam implantation process provides a superadherent, substantially pinhole-free coating 32 over the exposed surfaces of the bracket. Application of the silicon dioxide layer by deposition may be performed under vacuum conditions on the order of $1 \times 10^{-7}$ Torr. It is believed that the high energy application of silicon dioxide ions causes the ions to mix with the surface atoms of the bracket to form an extremely high-strength bond therewith. This high energy surface treatment provides a thin, uniform coating on the order of 5000 Å in thickness. Thus, the overall bond strength characteristics of brackets 10 are further enhanced since the silicon dioxide layer is capable of chemically bonding with various dental adhesives.

Subsequent to application of the chemically activatable material ($SiO_2$), the brackets may be subjected to a suitable treatment which chemically activates the chemically activatable material. For example, silicon dioxide layer 39 (or the silicon dioxide coating over the entire bracket) may be subsequently activated by treatment with silane to further increase its chemical bonding characteristics and to further improve the overall bond strength of bracket 10. This silane activation, which serves to create chemical bonding sites, is preferably accomplished by immersion of the brackets in a silane solution (composition given below) heated to about 50°±5° C., for about 20 minutes (with periodic stirring). Thereafter, the brackets are sequentially washed with a 10% (by weight) isopropanol solution and de-ionized water. Finally, the brackets are dried in a forced draft oven at 110° C. A suitable silane solution has the following composition:

| Component (source) | Approximate Wt. % |
|---|---|
| gamma-methacryloxypropyltrimethoxy silane (Petrarch Silicones) | 3% |
| glacial acetic acid | 3% |
| de-ionized water | 2% |
| isopropyl alcohol | balance |

Other methods of applying the activatable material include sputtering, plasma coating and flame spraying the exposed surfaces of the bracket base 14 and the tooth facing surfaces 12. These alternative coating techniques are also well known procedures to persons skilled in the art.

Tables 1 and 2 below present a comparison of shear and tensile bond strengths for various coated and uncoated brackets. All brackets were bonded to bovine teeth using Ormco SEQUENCE adhesive. The brackets were then placed in water bath at 37° C. for about 24 hours prior to testing.

TABLE 1

TENSILE TEST OF POLYMER BRACKETS

| Sample | 1 With Projections S1 | 2 Without Projections A1 S1* | 3 Without Projections A2 S1* | 4 With Projections S1 + S2** | 5 With Projections A2 S1 + S2 | 6 Without Projections A2 S1 + S2 | 7 With Projections Stock | 8 Without Projections A1 Stock* | 9 Without Projections A2 Stock* |
|---|---|---|---|---|---|---|---|---|---|
| Avg. Tensile Load at failure (kg) | 5.28 | 0 | 0 | >8.08 | 4.66 | 3.75 | 4 | 0 | 0 |
| Std. Dev. kg | 1.35 | 0 | 0 | 0.39 | 2.19 | 0.92 | 0.5 | 0 | 0 |
| Min. Tensile Load at failure (kg) | 2.4 | 0 | 0 | 7.5 | 1.2 | 1.5 | 2.9 | 0 | 0 |
| Max. Tensile Load at failure (kg) | 7.1 | 0 | 0 | 8.7 | 7.4 | 4.6 | 4.6 | 0 | 0 |

TABLE 1-continued

TENSILE TEST OF POLYMER BRACKETS

| Sample | 1<br>With<br>Projections<br>S1 | 2<br>Without<br>Projections<br>A1<br>S1* | 3<br>Without<br>Projections<br>A2<br>S1* | 4<br>With<br>Projections<br>S1 + S2** | 5<br>With<br>Projections<br>A2<br>S1 + S2 | 6<br>Without<br>Projections<br>A2<br>S1 + S2 | 7<br>With<br>Projections<br>Stock | 8<br>Without<br>Projections<br>A1<br>Stock* | 9<br>Without<br>Projections<br>A2<br>Stock* |
|---|---|---|---|---|---|---|---|---|---|
| Tensile Load at Failure | 100% | 100% | 100% | 0% | 100% | 100% | 100% | 100% | 100% |

S1: is referred to the brackets that were coated with $SiO_2$.
S2: is referred to the brackets that were coated with $SiO_2$ and then silanated.
*These brackets debonded from the enamel during ligation, hence no load is associated with their failure.
**Six of the brackets did not have bond failures, but the wing broke. The average of the load has taken the Max. load at which the wings failed into consideration.
A1 (Area 1) < A2 (Area 2)

TABLE 2

SHEAR TESTING OF POLYMER BRACKETS

| Sample | 1<br>Without<br>Projections<br>S1 | 2<br>Without<br>Projections<br>A2<br>Si | 3<br>Without<br>Projections<br>A2<br>S1 | 4<br>With<br>Projections<br>S1 + S2 | 5<br>Without<br>Projections<br>A1<br>S1 + S2 | 6<br>Without<br>Projections<br>A2<br>S1 + S2 | 7<br>With<br>Projections<br>Stock | 8<br>Without<br>Projections<br>A1<br>Stock | 9<br>Withouth<br>Projections<br>A2<br>Stock |
|---|---|---|---|---|---|---|---|---|---|
| Avg. Shear Load at failure (kg) | 8.75 | 5.26 | 6.19 | 12.14 | 10.24 | 10.82 | 8.78 | 4.29 | 3.01 |
| Std. Dev. (kg) | 1.94 | 1.7 | 2.51 | 1.8 | 4.08 | 3.39 | 1.16 | 2.38 | 3.07 |
| Min. Shear Load at failure (kg) | 6.3 | 2 | 2.8 | 9.4 | 7.1 | 6.8 | 6.4 | 0 | 0 |
| Max. Shear Load at failure (kg) | 11.9 | 7.5 | 9.7 | 15.9 | 18.8 | 16.3 | 10.7 | 9.9 | 8.2 |
| Adhesive Remaining on tooth at failure (%) | 93% | 100% | 100% | 0% | 64% | 93% | 89% | 100% | 100% |

S1: is referred to the brackes that were coated with $SiO_2$.
S2: is referrred to the brackets that were coated with $SiO_2$ and then silanated.
A1 (Area 1) < A2 (Area 2)

Figure 10:
FIG. 10 is a photomicrograph of a typical wing failure during tensile testing wherein the bracket remains adhered to the surface of the tooth.
Figure 11:
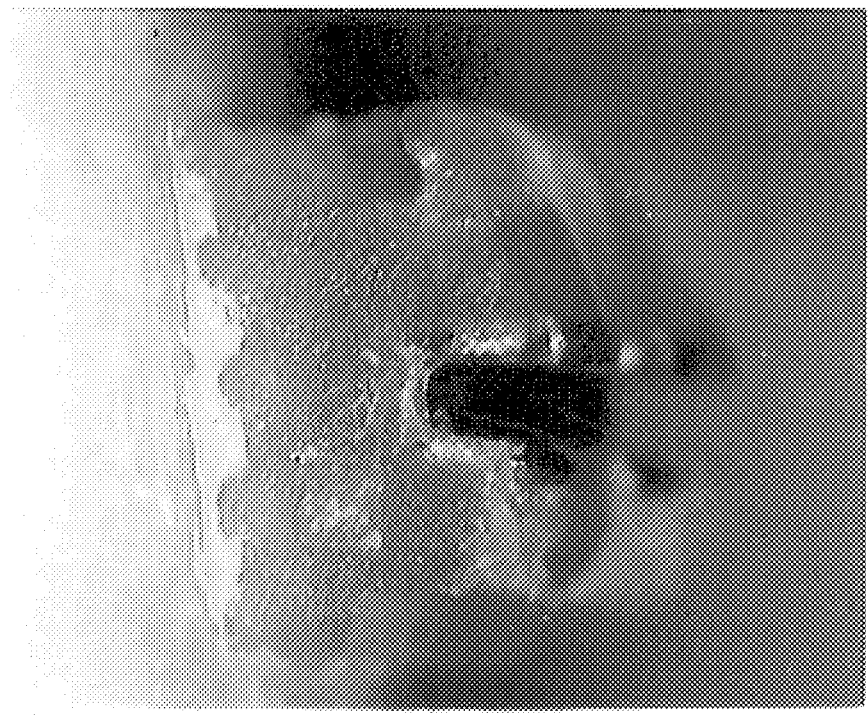
FIG. 11 is a photomicrograph of yet another example of gingival wing failure, wherein the bracket remains adhered to the surface of the tooth.

Tensile bond strength of polymer brackets with undercut projections after $SiO_2$ coating and silanation (treated) was improved by 53%. The brackets demonstrated 60% wing failure during tensile testing of the present invention while the bond between the bracket and the enamel was still intact. FIGS. 10 and 11 represent typical wing fractures during tensile testing. It can be seen that the brackets are still mounted on the teeth.

The minimum load for bond failure in tensile mode was improved by 216%, from 2.4 kg or 7.5 kg. Tensile bond strength distribution for the treated brackets with undercut projections was significantly narrowed. The standard deviation was 0.3 a kg for treated and 1.35 kg for untreated brackets.

Figure 12:
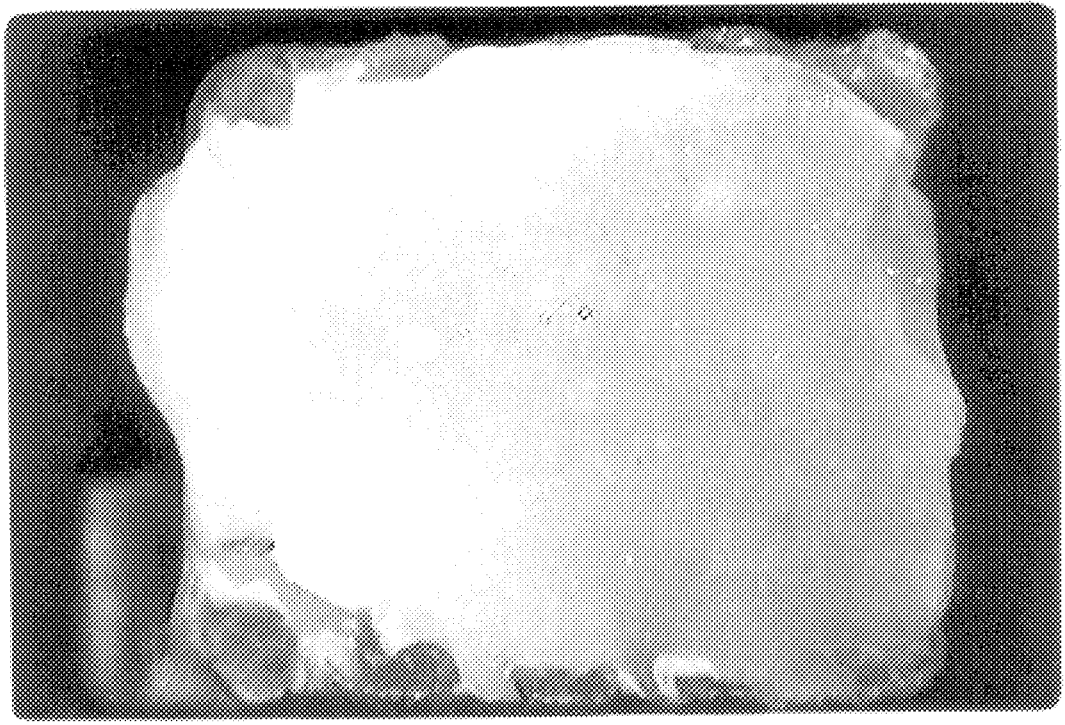
FIG. 12 is a photomicrograph of the treated bracket of the present invention following tensile bond failure, wherein essentially all adhesive remains on the bracket.
Figure 13:
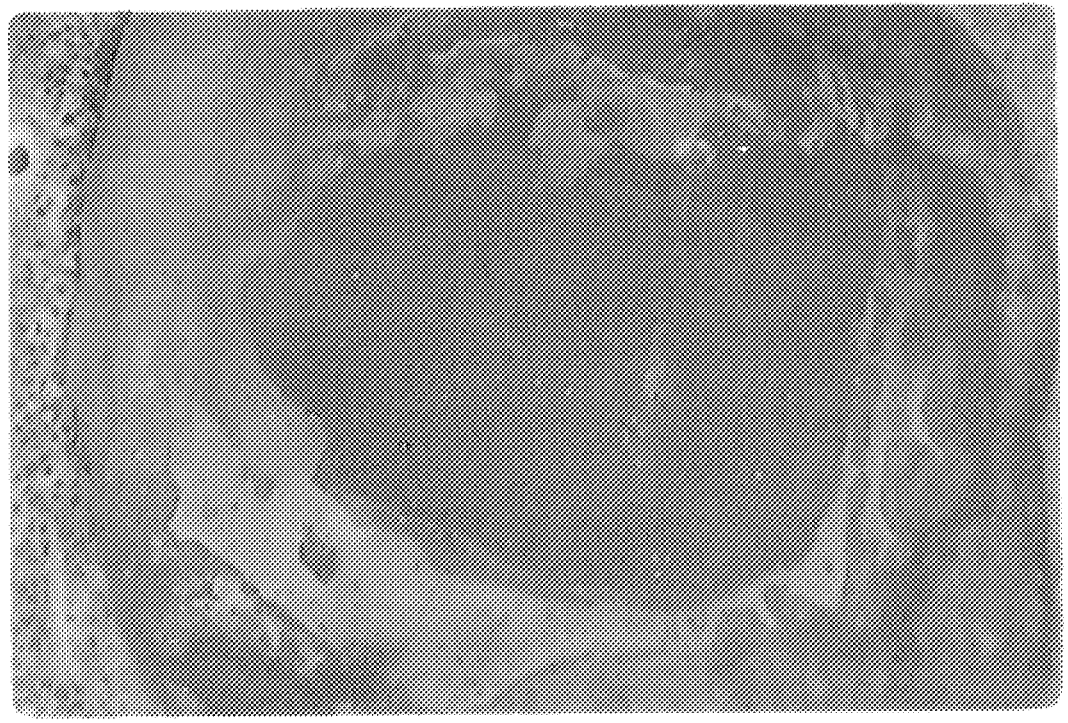
FIG. 13 is a photomicrograph of the tooth enamel surface after the bracket of FIG. 12 has been removed, wherein the enamel surface under the bracket is essentially free of adhesive.
Figure 14:
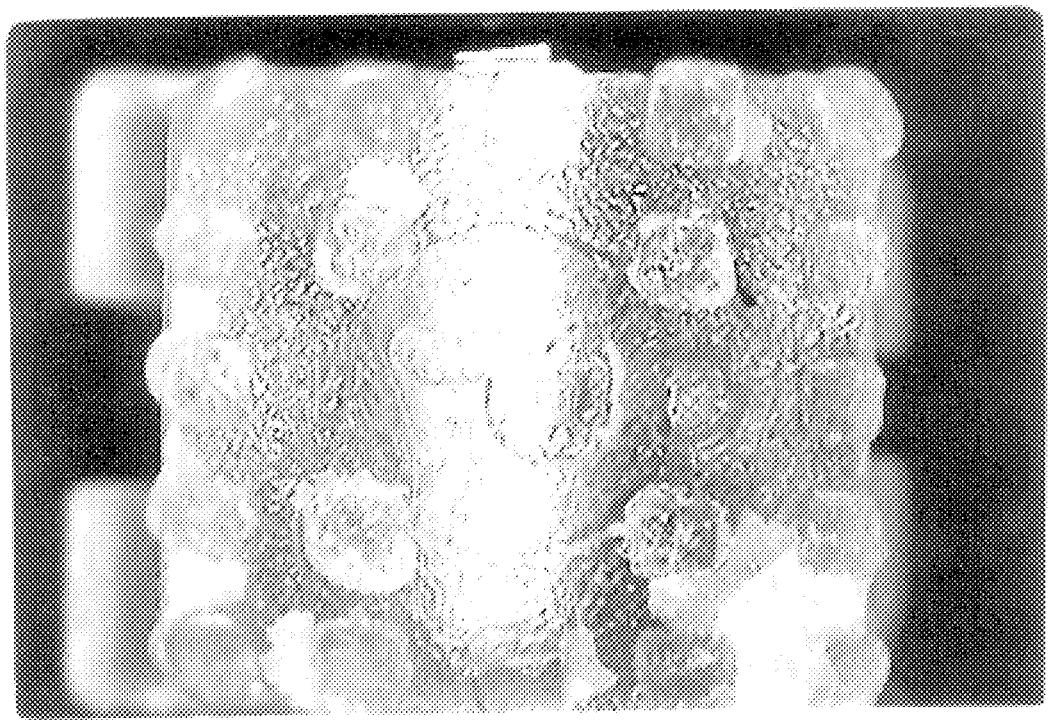
FIG. 14 is a photomicrograph of a typical polymer-based orthodontic appliance having undercut regions following tensile bond failure, wherein essentially no adhesive remains on the bracket.
Figure 15:
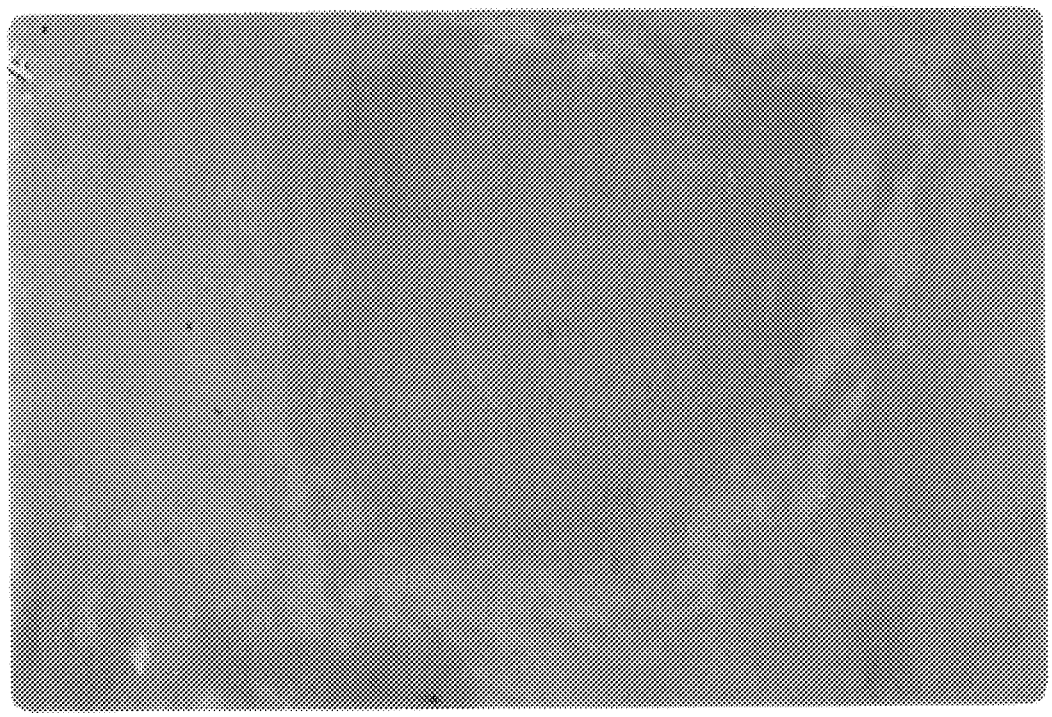
FIG. 15 is a photomicrograph of the tooth enamel surface after removal of the appliance of FIG. 14, wherein essentially all adhesive remains on the enamel surface.

In all cases of shear and tensile failures, treated brackets with undercut projections removed substantially all of the adhesive from the enamel upon debonding. FIGS. 12 and 13 demonstrate a typical debonded treated bracket and enamel. It can be seen that the enamel surface is the weakest bonding surface. Nontreated brackets left an average of about 90% of the adhesive on the enamel.

Shear bond strength of the treated brackets with undercut projections was improved by 38% over untreated brackets. All the adhesive was removed by the enamel surface and stayed with the bracket following the bond failure in shear mode.

It is to be understood that various changes and modifications may be made to the preferred embodiments discussed above without departing from the scope of the present invention, which is defined by the following claims and equivalents thereof.

I claim:

1. An orthodontic appliance having improved bonding characteristics when bonded to a tooth surface, comprising:
   a polymeric base having projecting structure extending outwardly from said base, said projecting structure having an inner extremity integrally connected to said base, and an outer extremity, said outer extremity having a cross-sectional area greater than the cross-sectional area of the inner extremity, thereby defining undercuts in said projecting structure proximate said outer extremity to facilitate mechanical bonding of said orthodontic appliance to a tooth surface with an adhesive; and
   a bond strength enhancement coating applied to at least said projecting structure.

2. The orthodontic appliance of claim 1, wherein said bond strength enhancement coating is a chemically activatable material.

3. The orthodontic appliance of claim 2, wherein said bond strength enhancement coating is $SiO_2$.

4. The orthodontic appliance of claim 2, wherein said bond strength enhancement coating comprises an oxide of an element selected from the group consisting of silicon, boron, titanium, magnesium, aluminum, zirconium, potassium, calcium, and sodium.

5. The orthodontic appliance of claim 2, wherein said chemically activatable material is activated by treatment with silane.

6. The orthodontic appliance of claim 1, wherein said bond strength enhancement coating is applied by sputtering.

7. The orthodontic appliance of claim 1, wherein said bond strength enhancement coating is applied by plasma coating.

8. The orthodontic appliance of claim 1, wherein said bond strength enhancement coating is applied by ion beam deposition.

9. The orthodontic appliance of claim 1, wherein said base includes a thermoplastic material.

10. The orthodontic appliance of claim 9, wherein said thermoplastic is polycarbonate.

11. The orthodontic appliance of claim 9, wherein said thermoplastic is a glass-filled reinforced polycarbonate.

12. A method of enhancing the bonding characteristics of an orthodontic appliance comprising a polymeric base with projecting structure having an inner extremity integrally connected to said base, and an outer extremity, said outer extremity having a cross-sectional area greater than the cross-sectional area of the inner extremity, said method comprising:

applying a bond strength enhancement coating to at least said projecting structure.

13. The method of claim 12 wherein said bond strength enhancement coating is a chemically activatable material.

14. The method of claim 13 wherein said bond strength enhancement coating is $SiO_2$.

15. The method of claim 13, wherein said bond strength enhancement coating is an oxide of an element selected from the group consisting of silicon, boron, titanium, magnesium, zirconium, aluminum, potassium, calcium, and sodium.

16. The method of claim 13 further comprising the step of chemically activating said bond strength enhancement coating.

17. The method of claim 16 wherein said bond strength enhancement coating is activated by treatment with silane.

18. The method of claim 12, wherein said bond strength enhancement coating is applied by plasma coating.

19. The method of claim 12, wherein said bond strength enhancement coating is applied by ion beam deposition.

20. The method of claim 12, wherein said bond strength enhancement coating is applied by sputtering.

* * * * *